United States Patent [19]
Ogle et al.

[11] Patent Number: 5,958,669
[45] Date of Patent: Sep. 28, 1999

[54] APPARATUS AND METHOD FOR CROSSLINKING TO FIX TISSUE OR CROSSLINK MOLECULES TO TISSUE

[75] Inventors: Matthew F. Ogle, St. Paul; Richard F. Schroeder, Oakdale, both of Minn.

[73] Assignee: St. Jude Medical, Inc., St. Paul, Minn.

[21] Appl. No.: 08/850,361

[22] Filed: May 2, 1997

[51] Int. Cl.$^6$ .............................. A01N 1/02; A61F 2/00; G01N 1/30; C12N 11/02
[52] U.S. Cl. ...................... 435/1.1; 424/423; 424/520; 435/40.52; 435/174; 435/177; 435/325; 435/366; 530/402; 530/810; 530/812
[58] Field of Search ................... 435/1.1, 40.52, 435/174, 177, 181, 325, 366; 530/356, 402, 810, 812; 424/423, 520

[56] References Cited

U.S. PATENT DOCUMENTS

| | | | |
|---|---|---|---|
| 3,966,401 | 6/1976 | Hancock et al. | 8/94.11 |
| 4,050,893 | 9/1977 | Hancock et al. | 8/94.11 |
| 4,120,649 | 10/1978 | Schechter | 8/94.11 |
| 4,399,123 | 8/1983 | Oliver et al. | 424/95 |
| 4,624,822 | 11/1986 | Arru et al. | 264/544 |
| 4,725,671 | 2/1988 | Chu et al. | 530/356 |
| 4,729,139 | 3/1988 | Nashef | 8/94.11 |
| 4,755,593 | 7/1988 | Lauren | 530/356 |
| 4,798,611 | 1/1989 | Freeman, Jr. | 623/66 |
| 4,800,603 | 1/1989 | Jaffe | 8/94.11 |
| 4,813,964 | 3/1989 | Dixon et al. | 623/13 |
| 5,769,780 | 6/1998 | Hata et al. | 600/36 |

FOREIGN PATENT DOCUMENTS 0 411 925 A2  2/1991  European Pat. Off. .
0 457 430 A2  11/1991  European Pat. Off. .

OTHER PUBLICATIONS

Cheung et al., Connective Tissue Research, vol. 13, pp. 109–115 (1985).

Cheung et al., Connective Tissue Research, vol. 10, pp. 201–216 (1982).

Aubrey Woodroof, Shiley Scientific, Inc., pp. 1–3 (1978).

"Hybrid Biomaterials based on the Interaction of Polyurethane Oligomers with Porcine Pericardium" by, Wen Keong Loke et al. Biomaterials 1996, vol. 17 No. 22 pp. 2163–2172.

*Primary Examiner*—David M. Naff
*Attorney, Agent, or Firm*—Westman, Champlin & Kelly, P.A.; Peter S. Dardi; Hallie A. Finucane

[57] ABSTRACT

Crosslinking to prepare fixed tissue or to crosslink modification molecules to tissue is carried out with an apparatus and method wherein diffusion through a semipermeable is used to provide a selected molecular weight distribution of oligomers of a crosslinking compound that polymerizes spontaneously in solution to produce oligomers such as glutaraldehyde. The membrane has a molecular weight exclusion limit that prevents oligomers above a certain molecular weight from passing. Tissues treated with the size selected oligomers have improved properties. In the apparatus, the membrane separates a solution containing the crosslinking compound and oligomers from a solution in which crosslinking is carried out. The selected molecular weight distribution of oligomers diffuses through the membrane into the solution where tissue is crosslinked or a beneficial molecule is crosslinked to tissue.

20 Claims, 2 Drawing Sheets

APPARATUS AND METHOD FOR CROSSLINKING TO FIX TISSUE OR CROSSLINK MOLECULES TO TISSUE

FIELD OF THE INVENTION

The invention relates to tissue fixation with crosslinking compounds selected to crosslink tissue in an improved fashion. The invention further relates to an apparatus for preparing the crosslinking compounds and for contacting the tissue with crosslinking compounds.

BACKGROUND OF THE INVENTION

A variety of bioprostheses incorporate tissue as at least a component of the prosthesis. Such bioprostheses are used to repair or replace damaged or diseased organs, tissues and other structures in humans and animals. Tissue used in bioprostheses typically is chemically modified or fixed prior to use. Fixation stabilizes the tissue, especially from enzymatic degradation, and reduces the antigenicity. Bioprostheses must also be biocompatible due to prolonged contact with bodily fluids and/or tissues.

Typical fixation agents act by chemically crosslinking portions of the tissue, especially collagen fibers. Crosslinking compounds include, for example, dialdehydes such as glyoxal and glutaraldehyde, carbodiimides, epoxies and oxidative fixation compounds such as photoxidative fixation agents. Glutaraldehyde particularly is preferred in part because it can be used at an approximately physiological pH under aqueous conditions. In addition to crosslinking the tissue, glutaraldehyde sterilizes the tissue and reduces the antigenicity of the tissue by the recipient.

While appropriate fixation of the tissue is critical, fixation generally is associated with decreased flexibility of the tissue. Also, fixation with glutaraldehyde has been associated with calcification, i.e., the deposit of calcium salts, especially calcium phosphate (hydroxyapatite), following implantation in a recipient. This is probably due to cytotoxicity resulting in necrosis of tissue leading to calcification. Calcification affects the performance and structural integrity of bioprosthetic devices constructed from these tissues, especially over extended periods of time. For example, calcification is the primary cause of clinical failure of bioprosthetic heart valves.

SUMMARY OF THE INVENTION

Selection of the appropriate distribution of oligomers of crosslinking compounds improves the characteristics of the fixed tissue. The oligomer distribution is selected by diffusion through a semipermeable membrane. The tissue treated by crosslinking with appropriately size-selected oligomers more closely resembles native tissue in appearance. Additionally, the tissue is naturally pliable to the touch rather than stiff. This flexibility of the tissue improves the mechanical performance of the tissue.

In a first aspect, the invention features an apparatus having:
  a) a source solution including a crosslinking compound; and
  b) a semipermeable membrane at least partially in contact with the source solution, the semipermeable membrane isolating a crosslinking solution from the source solution except by way of passage through the semipermeable membrane.

The semipermeable membrane preferably restricts passage of molecules, the membrane having a molecular weight exclusion limit of no more than about 10,000 daltons. The molecular weight exclusion limit is more preferably no more than about 7,500 daltons, or no more than about 5,000 daltons, or no more than about 1,000 daltons. The semipermeable membrane can comprise a dialysis membrane. The source solution preferably includes an aqueous glutaraldehyde solution with a concentration of glutaraldehyde from about 0.1 to about 50 percent by weight, and more preferably from about 0.5 percent to about 10 percent by weight.

The apparatus further can include a device within the crosslinking solution, the device including tissue. The semipermeable membrane can form a closed surface, wherein the inside volume defined by the closed surface contains the crosslinking solution. Alternatively, the semipermeable membrane can form a closed surface, wherein the inside volume defined by the closed surface contains the source solution. In another embodiment, the semipermeable membrane forms an open surface dividing two portions of a container, where the source solution is located on one side of the open surface and the crosslinking solution is located on the opposite side of the open surface.

In another aspect, the invention features a method of fixing tissue including contacting a tissue with a crosslinking solution comprising a crosslinking compound and oligomers thereof. The crosslinking compound and oligomers thereof enter the crosslinking solution by passing through a semipermeable membrane from a source solution comprising the crosslinking compound. The source solution preferably includes an aqueous glutaraldehyde solution with a concentration of glutaraldehyde from about 0.1 percent to about 50 percent by weight. In one embodiment, the tissue forms at least a portion of a bioprosthetic heart valve. The source solution preferably is approximately at equilibrium with respect to the size distribution of crosslinking compound oligomers prior to initiation of diffusion through the semipermeable membrane.

In another aspect, the invention features a method of crosslinking a modification molecule to a tissue by contacting both the tissue and the molecule together with a crosslinking solution including a crosslinking compound and oligomers thereof. The crosslinking compound and oligomers thereof enter the crosslinking solution by diffusing through a semipermeable membrane from a source solution comprising the crosslinking compound.

In another aspect, the invention features a fixed tissue including tissue having crosslinks with crosslinking compound and oligomers thereof. The crosslinking compound and oligomers thereof have a molecular weight distribution determined by diffusion through a semipermeable membrane in contact with an aqueous, source solution comprising from about 0.5 percent by weight to about 10 percent by weight crosslinking compound, the semipermeable membrane being permeable to molecules with a molecular weight less than about 20,000 daltons. Preferably, the source solution is approximately at equilibrium with respect to size distribution of crosslinking compound oligomers prior to initiation of diffusion through the semipermeable membrane.

DESCRIPTION OF THE PREFERRED EMBODIMENTS

Figure 1:
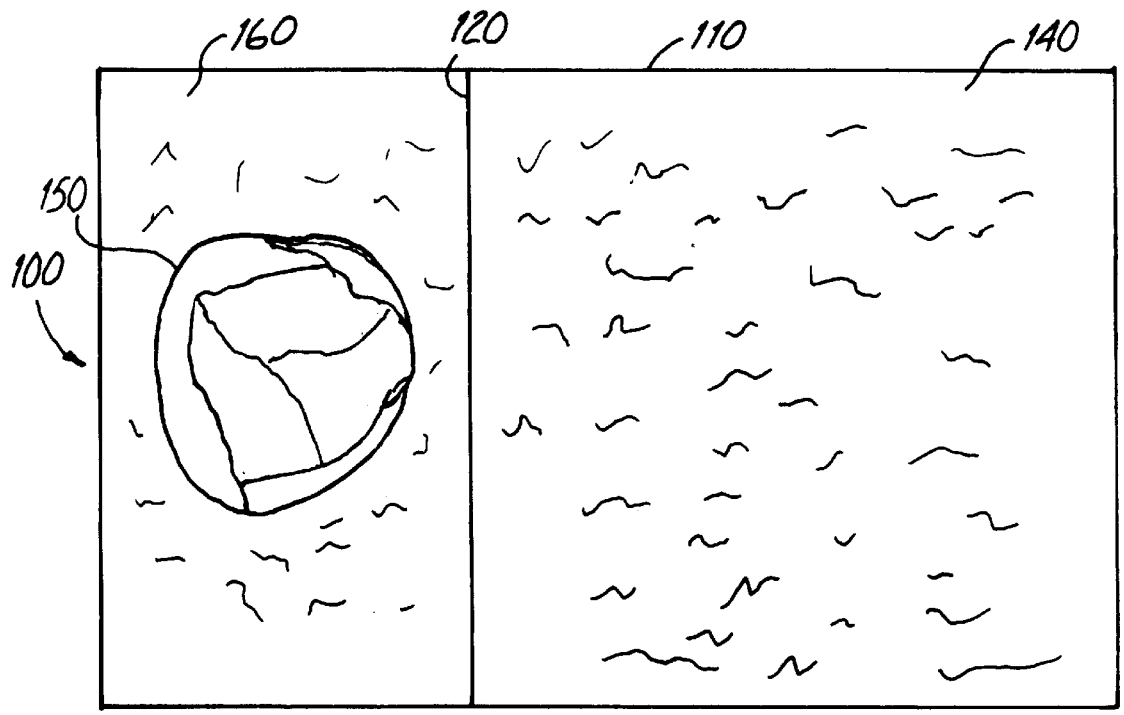
FIG. 1 is a top view of a first embodiment of an apparatus of the invention.

Crosslinking compounds, such as dialdehydes, can polymerize spontaneously in solution under a variety of conditions. Selection of crosslinking compound oligomers within a preferred range of molecular weights improves the characteristics of the fixed tissue. The oligomer weight distribution preferably is determined by diffusion through a semipermeable membrane. When the polymerization process is appropriately controlled, a significant fraction of the diffusing oligomers can crosslink the tissue before polymerization produces significantly more large oligomers.

An apparatus is presented to perform this selective crosslinking. The apparatus includes a container to hold relevant solutions and a semipermeable membrane to perform the size selection. Tissues treated with the size selected crosslinking compound oligomers have improved properties. The selected oligomers of the crosslinking compound can be used to fix tissue and/or to attach modification molecules to tissue.

A. Tissue and Bioprostheses

The tissue to be crosslinked generally forms at least part of a medical device, generally a bioprosthesis. Appropriate bioprostheses include, for example, artificial hearts, heart valves, pericardial patches, vascular grafts, biological conduits, skin patches, ligament repair material, surgical patches and tendons. The bioprostheses may or may not include components other than the tissue. The tissue can be crosslinked prior to formation into the bioprosthesis or following formation into the bioprosthesis.

Nontissue components of the bioprosthesis can be formed from a variety of other biocompatible materials such as metals, ceramics and polymers. Appropriate polymers include, for example, hydrogels, reabsorbable polymers and nonreabsorbable polymers. These nontissue components can take the form of, for example, stents, cloth covers, sewing cuffs or sutures.

Appropriate tissues include intact tissue as well as decellularized tissue. These tissues may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura matter; skin; bone; umbilical tissues; and the like.

Natural tissues are derived from a particular animal species, typically mammalian, such as human, bovine, porcine, seal or kangaroo. These natural tissues generally include collagen-containing material. Natural tissue is typically, but not necessarily, soft tissue.

Appropriate tissues also include tissue equivalents such as a tissue-engineered material involving a cell-populated matrix, which can be formed from a polymer, biopolymers or from a decellularized natural tissue. Biopolymers can be naturally occurring or produced in vitro. Purified biological polymers can be appropriately formed into a substrate by techniques such as weaving, knitting, casting, molding, extrusion, cellular alignment and magnetic alignment.

B. Crosslinking Compounds

The crosslinking compounds include a variety of organic compounds typically with two or more functional groups. Particularly preferred crosslinking compounds include dialdehydes. Preferred dialdehydes include, for example, glutaraldehyde, malonaldehyde, glyoxal, succinaldehyde, adipalaldehyde, phthalaldehyde and derivatives thereof. Derivatives of glutaraldehyde include, for example, 3-methylglutaraldehyde and 3-methoxy-2,4-dimethyl glutaraldehyde. Dialdehydes tend to polymerize spontaneously at conditions appropriate for crosslinking tissue, i.e., in aqueous solutions at approximately physiological pHs and physiological temperatures. Spontaneous polymerization can be controlled by appropriate selection of temperature, pH and/or atmospheric control. Polymers that do form can be selected for size through the use of membranes. Efficiency of this selection can be enhanced by varying transmembrane pressure.

The crosslinking compounds preferably are supplied in an aqueous source solution, as described further below.

C. Apparatus

An appropriate apparatus for the treatment of tissue generally has at least one container for holding liquid, and a semipermeable membrane. The semipermeable membrane divides two volumes formed within the container or containers. The two volumes are isolated from each other except for possible flow or diffusion through the semipermeable membrane. One of the two volumes holds a source solution that provides the crosslinking compound. The second volume holds a crosslinking solution along with the device to be crosslinked. The crosslinking solution includes a quantity of crosslinking compound and oligomers of the crosslinking compound that have diffused through the semipermeable membrane.

The apparatus can be configured in a variety of ways. In one embodiment shown in FIG. 1, the apparatus 100 has a container 110 and a generally planar, semi-permeable membrane 120 dividing the container 110. The container 110 on one side of membrane 120 holds the source solution 140 while the container on the other side of membrane 120 holds the tissue(s)/device(s) 150 and the crosslinking solution 160. Appropriate stirring can be provided as desired.

The container can be made from a variety of materials, such as glass, metals or polymers, or a combination of materials. Suitable materials generally are inert with respect to the source solution and the crosslinking solution.

The container can have any shape desired as long as diffusion through one or more semipermeable membranes provides the only connection for liquid flow between the source solution and the crosslinking solution. For example, the container can narrow at the point of contact between the source solution and the crosslinking solution. Similarly, the membrane or membranes can take any desired shape as long as a surface or surfaces formed by the membrane(s) separate the source solution and the crosslinking solution such that no molecules from the liquids can flow from one solution to the other without passing through a semipermeable membrane.

The use of pressure across the semipermeable membrane can enhance or speed up the delivery of the appropriate oligomers by driving fluid across the membrane. Furthermore, a series of membranes can be used with decreasing molecular weight permeability to improve the efficiency of the oligomer selection. The proximity of the membranes to each other can be adjusted, as desired. Also, the liquid from the source solution can be pumped through tubing into the crosslinking solution, where the membrane is located along the flow of the tubing. The source solution can be completely contained within the tubing.

Figure 2:
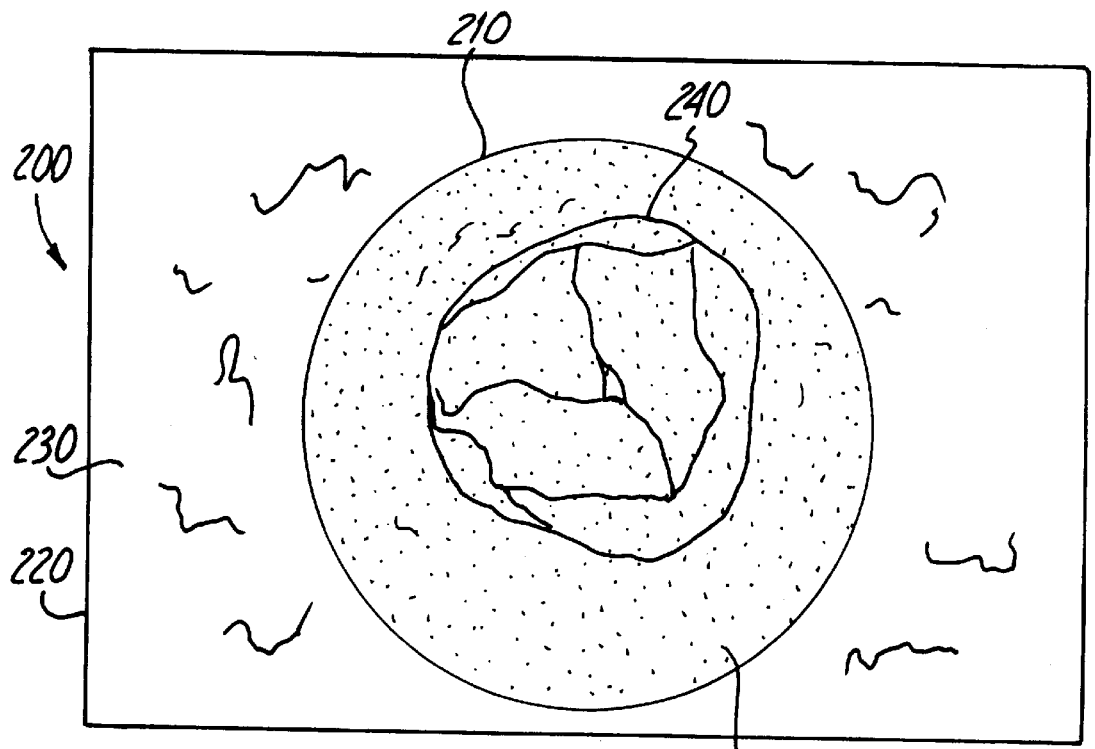
FIG. 2 is a top view of a second embodiment of an apparatus of the invention.

In another embodiment, the membrane 210 of apparatus 200 forms a closed surface, as depicted in FIG. 2. The container 220 holds the source solution 230. The tissue/device 240 is located within semipermeable membrane 210 along with the crosslinking solution 250. Membrane 210 is located within the source solution 230 such that appropriate sized oligomers of the crosslinking compound can pass through membrane 210 between solutions 230, 250. Apparatus 200 can include a plurality of membranes 210 each containing a crosslinking solution 250 and one or more units of tissue/device 240.

Figure 3:
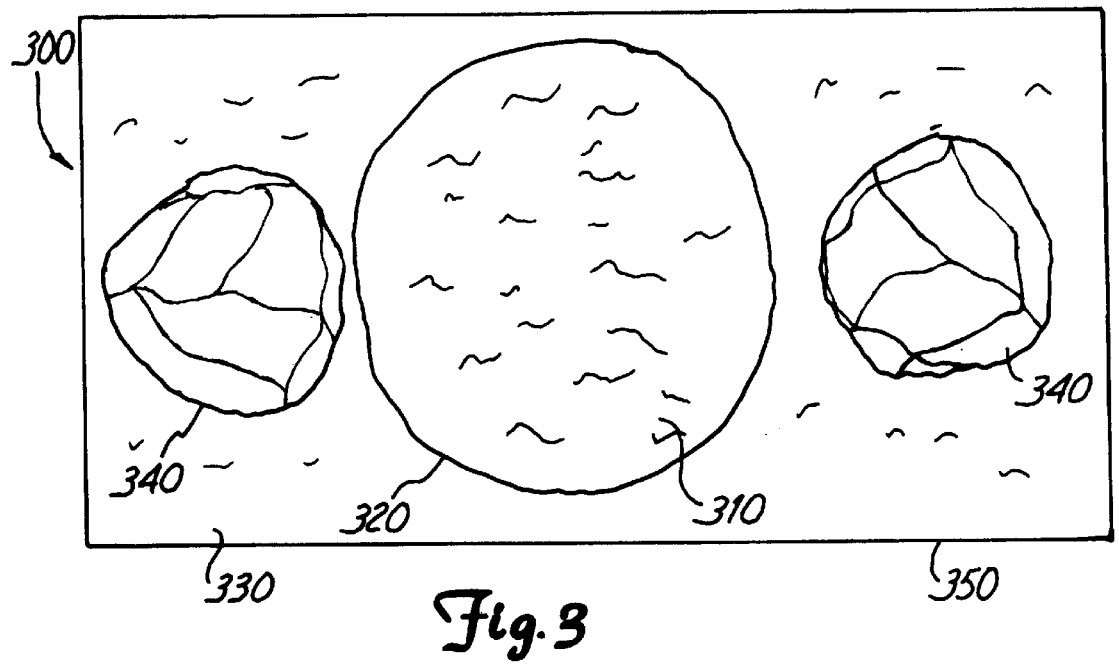
FIG. 3 is a top view of a third embodiment of an apparatus of the invention.

Referring to FIG. 3, in another embodiment of the apparatus 300, source solution 310 is placed within a closed, semipermeable membrane 320. Crosslinking solution 330 and one or more units of tissue/device 340 are placed in container 350. Membrane 320 is located within crosslinking solution 330 such that oligomers of the crosslinking compound can pass between solutions 310, 330 through membrane 320. Additional membranes containing source solution can be used, if desired.

Variations on these embodiments of the apparatus also can be used. Whatever embodiment is selected, it generally is preferable for the volume of the source solution to be larger than the volume of the crosslinking solution. Having a larger volume of source solution reduces the fluctuations in the distribution of molecular weights of the crosslinking compound oligomers within the crosslinking solution. More uniform results generally result from a more uniform distribution of molecular weights.

A significant feature of the semipermeable membrane is its ability to select an appropriate distribution of crosslinking compound oligomers. The membrane generally is microporous such that complexes greater than a certain size cannot pass through the membrane. The membrane can be made from a variety of materials including, for example, various polymers, metals and ceramic materials. Polymeric membranes generally are preferred because of their ease of handling. Preferred polymers for producing the membrane include, for example, nylon, polysulfone, cellulose acetate, cellulose triacetate and polypropylene. Dialysis tubing and comparable materials are convenient because of their ready availability and suitable characteristics. Polymeric membranes are also useful in pressurized (i.e., reverse osmosis) systems.

Appropriate porous material generally is described by a pore size in terms of the molecular weight of approximately the largest compound that can pass through the pores. The physical size of the pores through the membrane is only one of the factors that determine the diffusion through the membrane. The chemical and physical characteristics of the compositions can also influence diffusion through the membrane. These characteristics include polarity and hydrophobicity.

In addition to forming oligomers, the crosslinking compounds may associate in other ways not involving chemical bonding that also may affect diffusion through the membrane. It may not always be possible to estimate accurately the distribution of oligomers passing through the membrane based solely on the pore size of the membrane. Nevertheless, the pore size distribution of the membrane certainly is related to the size of the oligomers passing through the membrane. Some empirical adjustment may be needed for particular membranes and crosslinking compounds.

Following standard usage, pore sizes recited herein are based on the molecular weight of the largest compound of any chemical nature that can pass through the pore. For glutaraldehyde and a dialysis membrane made from cellulose acetate, the pores preferably have an average exclusion limit from about 100 daltons to about 20,000 daltons, and more preferably from about 500 daltons to about 10,000 daltons and even more preferably from about 1000 daltons to about 5000.

The source solution contains a reservoir of crosslinking compound. The source solution preferably is buffered at a pH that will not result in damage to the tissue. The source solution is preferably buffered at a pH between about 6 to about 8, and more preferably about 6.3 to about 7.4. Preferred buffers do not harm the tissue and do not interfere with the crosslinking process. Suitable buffers can be based on, for example, the following compounds: phosphate, borate, bicarbonate, carbonate, cacodylate, citrate, and other organic buffers such as tris(hydroxymethyl)aminomethane (TRIS), N-(2-hydroxyethyl) piparazine-N'-(2-ethanesulfonic acid) (HEPES) or morpholine propanesulphonic acid (MOPS). The source solution also can include salts to adjust the ionic strength preferably to a near physiological ionic strength. Ringer's solution can be used to provide appropriate buffering and ionic strength.

The concentration of crosslinking compound within the source solution affects the oligomer distributions within the crosslinking solution. Therefore, the distribution of oligomers diffusing through the membrane is altered by the concentration of the source solution. The source solution preferably is at or near equilibrium with respect to distribution of oligomers at the temperature and pH used for crosslinking. The temperature for crosslinking is preferably from about 4° C. to about 37° C., and more preferably from about 15° C. to about 25° C.

The concentration of the crosslinking compound in the source solution is selected to yield a desired distribution of oligomer sizes. Lowering the concentration of crosslinking compound in the source solution reduces the quantity of undesirably large oligomers but produces a higher quantity of monomers and small oligomers. In certain circumstances, a high quantity of monomers and small oligomers may also be undesirable since these would be too small to connect collagen fibrils. Based on the average distance between collagen fibrils in tissue, glutaraldehyde oligomers connecting the fibrils would have about 5–6 monomers. Based on this analysis, a preferred distribution of glutaraldehyde oligomers would have a large number of oligomers having between 3 and 10 monomer units, or more preferably most oligomers having between 5–6 monomer units.

The conditions can be optimized empirically, based on the teachings herein, rather than relying on a theoretical analysis of the optimum oligomer size. Following crosslinking, the tissue preferably is flexible and fully crosslinked. Crosslinking of the tissue can be evaluated by one or more of several established criteria such as thermal stability (i.e., shrink temperature), digestibility by enzymes, amino acid analysis and mechanical properties such as extensibility, elasticity and tensile strength. Additionally, the character of crosslinking can be further evaluated through both in vivo and in vitro biocompatibility assessment.

In addition, the tissue preferably has reduced susceptibility to calcification following implantation. Since calcification has been associated with unreacted aldehyde functional groups, a determination of quantities of unreacted aldehyde functional groups may provide some indication of calcification susceptibility. More directly, calcification susceptibility can be evaluated empirically by examining calcification following in vivo implantation in an animal host.

Proper selection of concentration for the source solution can reduce the quantity of monomers and small oligomers from entering the crosslinking solution, if desired. At the same time, the semipermeable membrane excludes undesirably large oligomers that may be present in the source solution. In this way, the crosslinking solution can have a fairly narrow distribution of oligomers sizes centered near a desired oligomer size.

For glutaraldehyde, the source solution generally has a concentration from about 0.1 percent by weight to about 50 percent by weight, more preferably from about 0.1 percent by weight to about 10 percent by weight, and even more preferably from about 0.5 to about 3 percent by weight. For other crosslinking compounds, appropriate concentrations can be determined either from known properties of spontaneous polymerization or from empirical determinations based on examination of tissue crosslinked using different concentrations of source solution.

The crosslinking solution preferably begins as pure water, saline, buffer or buffer with saline. Appropriate buffers should buffer near a physiological pH and include buffers described above. The temperature of the crosslinking solution should also be adjusted to the appropriate temperature. As time progresses, crosslinking oligomers pass through the membrane from the source solution into the crosslinking solution. Other compositions may also pass through the membrane, such as solvent, any ions from the buffer and the like.

The overall concentration of the crosslinking compound in the crosslinking solution can be relatively high so that the crosslinking time need not be particularly long. Nevertheless, the distribution of oligomers can be effectively determined by the diffusion through the membrane for reasonable periods of time if the polymerization time is relatively long. The polymerization time depends on, for example, pH, temperature, concentration and transmembrane pressure.

After sufficient time, the distribution of the oligomers within the crosslinking solution becomes more similar to the distribution in the source solution. This may not be a concern as long as the tissue is sufficiently fixed by the desired molecular weight distribution of oligomers prior to the accumulation of large oligomers in the crosslinking solution. Once the tissue is crosslinked, it becomes relatively unaffected by contact with large crosslinker oligomers. Alternatively, the tissue is removed from the crossslinking solution before the crosslinking solution has had time to develop an inappropriate distribution of crosslinking oligomers. Preferably, the tissue is removed from the solution to restrict further molecular rearrangements after a reasonable period of time, for example, after about 6 days.

D. Crosslinking Compounds to Tissue

In addition to fixing tissue, the apparatuses of the invention can be used to attach molecules to tissue by crosslinking. To bind the molecules to the tissue, the tissue and molecules are placed together in a crosslinking solution. The crosslinking compound oligomers diffusing through the membrane then act to crosslink the molecules to the tissue. Fixation of the tissue can be accomplished simultaneously with the attachment of the molecules, or the tissue can be fixed prior to the crosslinking of the molecules to the tissue.

Figure 4:
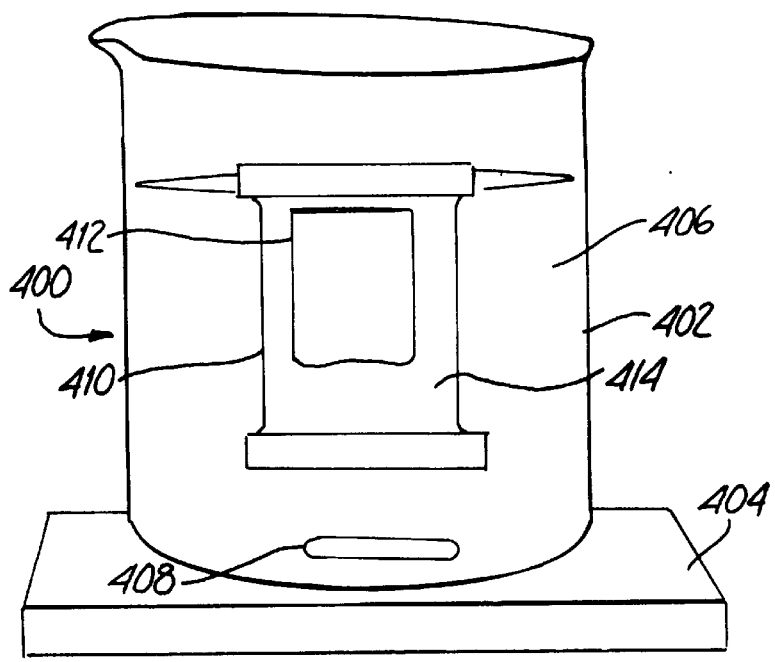
FIG. 4 is a side view of an apparatus of the invention appropriate for the crosslinking of a compound to a tissue.

An apparatus 400 for attaching the molecules to tissue is depicted in FIG. 4. A container 402 is located on a magnetic stirrer 404. The container holds a source solution 406 and a stir bar 408. The source solution 406 is comparable to the source solution described above for fixation. A closed membrane 410 is located within source solution 406.

Device 412 and crosslinking solution 414 are located within closed membrane 410. The crosslinking solution 414 includes monomers and oligomers of the crosslinking compound that have diffused through the membrane 410. Crosslinking solution 414 includes the molecule for attachment to device 412. Source solution 406 may or may not include the molecule for attachment. More than one medical device can be located within membrane 410, and more than one membrane 410 can be located within source solution 406. Variations on the apparatus such as those described above for fixation can be used for attaching molecules to the tissue.

Preferred compounds for attachment include, for example, proteins such as heparin, growth factors, adhesion molecules, anticalcifics, antithrombotics, antimicrobials, antioxidizers, chemotactants and other host response modifiers. Various forms of the protein ferritin or other metal binding proteins can be used to store metal cations. The ferritin molecules storing the metal cations can be bound to tissue to supply a source of metal cations at the tissue. Certain polyvalent metal cations, including $Al^{+3}$, $Mg^{+2}$ and $Fe^{+3}$, have been found to inhibit calcification. The use of proteins to store calcification inhibitors such as polyvalent metal cations is described in U.S. patent application Ser. No. 08/595,402 filed Feb. 5, 1996, now abandoned, and Ser. No. 08/690,661, filed Jul. 31, 1996, incorporated herein by reference. Other metal cations have antimicrobial activity, such as ions of Ag, Au, Pt, Pd, Ir, Cu, Sn, Sb, Bi and Zn. The use of proteins to store antimicrobial metal cations is described in U.S. patent application Ser. No. 08/787,139, filed Jan. 22, 1997, incorporated herein by reference.

E. Post Crosslinking Treatment

Following crosslinking as described above, the tissue can be stored prior to final sterilization. For example, the tissue may be stored at room temperature in normal saline or a 0.5 percent by weight glutaraldehyde solution buffered as described above. Other compounds such as an alcohol can be added to the storage solution. In addition, the tissue can be treated with anticalcification compositions or other compositions prior to storage or after storage.

The device comprising the tissue can be placed in a package along with packing material and appropriate labeling. Additional sterilization can take place prior to or following packaging. Radiation, chemicals and/or plasma can be used in the sterilization process. The packaged device is distributed to the appropriate medical personnel. The device incorporating the tissue preferably is rinsed in sterile saline solution prior to administration by medical personnel.

Practice of the present invention provides several advantages such as the following. The tissue treated by crosslinking with appropriately size-selected oligomers more closely resembles native tissue in appearance. Additionally, the tissue is naturally pliable to the touch rather than stiff. This flexibility of the tissue improves the mechanical performance of the tissue. Treatment with appropriately sized oligomers also results in better hemodynamics, improved functionality and improved biocompatibility.

EXAMPLE

This example demonstrates the effectiveness of treating tissue with a selective distribution of crosslinking agent oligomers.

A source solution was prepared starting with an aqueous, biological grade glutaraldehyde solution, 50 percent by weight solution of glutaraldehyde obtained from Electron Microscopy Sciences, Fort Washington, Pa. This solution was diluted with HEPES buffered, NaCl saline to form approximately 2.1 percent by weight glutaraldehyde solution. The 50 percent glutaraldehyde solution was diluted on a volume per volume basis with the final concentration being determined under standard practice in the field based on the assumption that the 50 percent stock solution and the diluent buffer have equal densities. A 800 ml portion of the 2.1 percent by weight glutaraldehyde solution was placed into a 1000 ml beaker.

A leaflet and an 8 mm diameter root punch were obtained from a porcine aortic heart valve and stored in saline. The leaflet and root punch were removed from the saline and placed into separate 10,000 dalton dialysis bags, cellulose ester membranes, Spectra/Por®, from Spectrum Medical Industries, Inc., Houston, Tex. The tissue punches and respective dialysis bags were placed into the beaker with the 2.1 percent glutaraldehyde solution. The beaker with the dialysis bag and glutaraldehyde solution were stored at room temperature for six days. After one day, a sample of solution was pipetted from the dialysis bag and found to contain 1.8 percent by weight glutaraldehyde as determined by HPLC.

After crosslinking, both tissue samples were white and pliable (perhaps slightly less pliable than uncrosslinked tissue) to the touch in comparison with comparable tissue crosslinked for equivalent periods of time in 2.0 percent glutaraldehyde solution, which are yellow and considerably less pliable. The shrink temperatures of the leaflet and root punch crosslinked in the dialysis bag were determined by Differential Scanning Calorimetry, Mettler TC 11, DSC 30 (Mettler, Highstown, N.J.). The root punch had a shrink temperature of 84.4 degrees and the leaflet had a shrink temperature of 83.6 degrees. Tissue treated by conventional crosslinking has a shrink temperature of 82–88. Conventional crosslinking, for example, involves crosslinking in an about 0.5 to about 2 percent by weight glutaraldehyde solution at room temperature buffered with a near physiological pH for three to seven days. Therefore, the root punch and leaflet crosslinked as described above are fully crosslinked.

Other embodiments of the invention are within the claims below.

What is claimed is:

1. An apparatus comprising:
   a) a source solution comprising a self-polymerizing crosslinking compound and oligomers thereof;
   b) a semipermeable membrane at least partially in contact with said source solution; and
   c) a second solution at least partially in contact with said membrane, said semipermeable membrane isolating said second solution from said source solution except by way of passage through said semipermeable membrane so that said crosslinking compound and oligomers thereof can pass across said membrane to provide in said second solution a distribution of oligomer sizes for crosslinking.

2. The apparatus of claim 1, wherein said membrane has a pore size that provides a molecular weight exclusion limit of no more than about 10,000 daltons.

3. The apparatus of claim 1, wherein said membrane has a pore size that provides a molecular weight exclusion limit of no more than about 7,500 daltons.

4. The apparatus of claim 1, wherein said membrane has a pore size that provides a molecular weight exclusion limit of no more than about 5,000 daltons.

5. The apparatus of claim 1, wherein said membrane has a Pore size that provides a molecular weight exclusion limit of no more than about 1,000 daltons.

6. The apparatus of claim 1, wherein said crosslinking compound comprises glutaraldehyde and oligomers thereof and said source solution comprises an aqueous glutaraldehyde solution with a concentration of glutaraldehyde from about 0.1 percent to about 50 percent by weight.

7. The apparatus of claim 1, further comprising a device within said second solution, said device comprising tissue.

8. The apparatus of claim 1, wherein said membrane forms a closed surface, wherein the inside volume defined by said closed surface contains said second solution.

9. The apparatus of claim 1, wherein said membrane forms a closed surface, wherein the inside volume defined by said closed surface contains said source solution.

10. The apparatus of claim 1, wherein said membrane forms an open surface dividing two portions of a container, where said source solution is located on one side of said open surface and said second solution is located on the opposite side of said open surface.

11. A method of fixing tissue comprising contacting a tissue with a crosslinking solution comprising a self-polymerizing crosslinking compound and oligomers thereof, said crosslinking compound and oligomers thereof within said crosslinking solution having passed through a semipermeable membrane from a source solution comprising said crosslinking compound and oligomers thereof to provide a distribution of oligomer sizes within said crosslinking solution.

12. The method of claim 11, wherein said membrane is permeable to molecules with a molecular weight no more than about 10,000 daltons.

13. The method of claim 11, wherein said membrane is permeable to molecules with a molecular weight no more than about 5,000 daltons.

14. The method of claim 11, wherein said membrane is permeable to molecules with a molecular weight no more than about 1,000 daltons.

15. The method of claim 11, wherein said crosslinking compound comprises glutaraldehyde and oligomers thereof and said source solution comprises an aqueous glutaraldehyde solution with a concentration of glutaraldehyde from about 0.1 percent to about 50 percent by weight.

16. The method of claim 11, wherein said tissue forms at least a portion of a bioprosthetic heart valve.

17. The method of claim 11, wherein said source solution is approximately at equilibrium with respect to distribution of sizes of oligomers of said crosslinking compound prior to initiation of passage through said semipermeable membrane.

18. A method of crosslinking a molecule to a tissue comprising contacting both said tissue and said molecule together with a crosslinking solution comprising a self-polymerizing crosslinking compound and oligomers thereof, said crosslinking compound and oligomers thereof within said crosslinking solution having diffused through a semipermeable membrane from a source solution comprising said crosslinking compound and oligomers thereof to provide a distribution of oligomer sizes within said crosslinking solution.

19. A fixed tissue comprising tissue having crosslinks comprised of a self-polymerizing crosslinking compound and oligomers thereof, said crosslinking compound and oligomers thereof having a molecular weight distribution determined by diffusion through a semipermeable membrane in contact with an aqueous, source solution comprising from about 0.5 percent by weight to about 10 percent by weight of said self-polymerizing crosslinking compound, said semipermeable membrane being permeable to molecules with a molecular weight no more than about 20,000 daltons.

20. The tissue of claim 19, wherein said source solution is approximately at equilibrium with respect to distribution of sizes of oligomers of said crosslinking compound prior to initiation of passage through said semipermeable membrane.

* * * * *